United States Patent [19]

Johnson et al.

[11] Patent Number: 4,931,286

[45] Date of Patent: Jun. 5, 1990

[54] HIGH GLOSS CELLULOSE TABLET COATING

[75] Inventors: Joseph L. Johnson, Newark; George W. Skinner, Wilmington, both of Del.

[73] Assignee: Aqualon Company, Wilmington, Del.

[21] Appl. No.: 340,757

[22] Filed: Apr. 19, 1989

[51] Int. Cl.[5] .................................................. A61K 9/36

[52] U.S. Cl. .......................................... 424/480; 427/3

[58] Field of Search ............................. 424/480; 427/3

[56] References Cited

U.S. PATENT DOCUMENTS

| | | | |
|---|---|---|---|
| 4,302,440 | 11/1981 | John et al. | 424/480 |
| 4,330,338 | 5/1982 | Banker | 424/480 |
| 4,513,019 | 4/1985 | Brancq et al. | 427/3 |
| 4,543,370 | 9/1985 | Porter et al. | 523/100 |
| 4,683,256 | 8/1987 | Porter et al. | 524/285 |
| 4,802,924 | 2/1989 | Woznicki et al. | 427/3 |

FOREIGN PATENT DOCUMENTS

| | | |
|---|---|---|
| 1217140 | 1/1987 | Canada . |
| 0253541 | 2/1987 | European Pat. Off. . |

OTHER PUBLICATIONS

Aqualon Technical Information Bulletin VC-556.

*Primary Examiner*—Thurman K. Page
*Attorney, Agent, or Firm*—James K. Luchs

[57] ABSTRACT

High gloss pharmaceutical tablets have an outer coating of sodium carboxymethylcellulose and polyethylene glycol as 0.1 to 5.0% by weight of the tablet. The sodium carboxymethylcellulose has a D.S. between 0.2 and 1.4 and a D.P. between 100 and 4000. Spraying the coating from a water solution eliminates the need for solvent recovery.

10 Claims, No Drawings

HIGH GLOSS CELLULOSE TABLET COATING

FIELD OF THE INVENTION

The invention relates to pharmaceutical tablets. In particular a sodium carboxymethylcellulose/plasticizer coating provides high gloss for such tablets.

BACKGROUND OF THE INVENTION

Coated tablets are well known in the pharmaceutical industry. In addition to pharmaceutical books, manuals and technical literature, patent publications in this field include: U.S. Pat. Nos. 4,543,370 and 4,683,256 on a tablet coating composition of methylcellulose or sodium ethylcellulose sulphate in water or alcohol; Canadian Patent 1,217,140 on a solvent coating composition comprising polyvinyl pyrrolidone, hydroxymethylcellulose, ethylcellulose, sodium lauryl sulphate and propylene glycol; European Patent Application 0 253 541 on a coating with a water permeable but water insoluble ethyl cellulose and dibutyl sebacate.

Aqualon Bulletin VC-556, *The Use of Klucel® Hydroxypropylcellulose, NF, To The Utility of Hydroxpropylmethylcellulose in Aqueous Film Coating,* describes how tablets coated from water solutions do not give high gloss such that a polishing coat step is used after the polymer coating in order to improve tablet appearance.

Film coating of pharmaceutical tablets have been carried out for years using organic solvents which provided high gloss finishes. With the move toward the use of water for tablet coatings to avoid the need for solvent recovery systems, it was observed that high gloss tablets could not be produced without the use of organic solvent.

SUMMARY OF THE INVENTION

A high gloss tablet comprises at least one active ingredient in a binder matrix as a core with an outermost coating of sodium carboxymethylcellulose having a degree of substitution (D.S.) between 0.2 and 1.4 and a degree of polymerization (D.P.) between 100 and 4000 and a plasticizer.

In a preferred tablet composition the active ingredient is pharmaceutically active, the plasticizer is polyethylene glycol and D.S. is between 0.5 and 0.9 and D.P. is between 200 and 1000 for sodium carboxymethylcellulose.

A method for preparing high gloss tablets comprises the steps:

(1) preparing an aqueous solution of sodium carboxymethylcellulose and a plasticizer; and (2) applying the solution to tablets to provide a weight gain of from 0.1 to 5.0% by weight.

In a preferred process the sodium carboxymethylcellulose has a D.S. between 0.5 and 0.9 and a D.P. between 200 and 1000, the plasticizer is polyethylene glycol and the weight gain of the tablet is 1.0 to 2.0%.

DETAILED DESCRIPTION OF THE INVENTION

It has been discovered that tablets coated with sodium carboxymethylcellulose from a water solution have a much higher gloss than with other cellulosic polymers. This discovery eliminates the need to increase the gloss by an additional coating. In addition only very small amounts of sodium carboxymethylcellulose are needed for these high gloss coatings, thus providing an unexpected economic advantage in terms of raw material costs and processing times. Furthermore, sodium carboxymethylcellulose films dissolve much more rapidly than films such as hydroxypropylmethylcellulose and thus are less likely to interfere with the dissolution of drug from a coated tablet.

Sodium carboxymethylcellulose is a cellulose gum available as AQUALON TM from the Aqualon Company as a 99.5% purity free flowing powder which meets all specifications of the U.S. PHARMACOPOEIA. For the purposes of the present invention the sodium carboxymethylcellulose must have a degree of substitution (D.S.) between 0.2 and 1.4 by carboxymethyl groups based on 3.0 as total substitution of available androhexoic sites, and the degree of polymerization (D.P.) must be between 100 and 400 for the cellulose polymer being substituted.

Sodium carboxymethylcellulose provides high gloss for a tablet when coated along with a plasticizer to give a weight gain to the tablet of from 0.1 to 5.0%. Preferably the range is 1.0 to 2.0%. It is not necessary that all of the polymer coating comprise sodium carboxymethylcellulose as long as there is sufficient quantity to provide the desired gloss.

A pharmaceutically approved plasticizer is used along with sodium carboxymethylcellulose as the primary components of the tablet coating composition in water. Polyethylene glycol with a molecular weight of about 400 is a preferred plasticizer. This material and other suitable plasticizers are available from Union Carbide Corporation.

Other ingredients which can be incorporated in the tablet coating include: colorants, opacifying materials, surfactants, stabilizers, silicas, silicones, preservatives, surface treatment agents, flavorants and other polymers deemed necessary and useful in promoting the utility, value and ease of preparation of the tablet or of coating the tablet.

In the following Example a spray apparatus known as Accela-Cota available from Thomas Engineering was employed wherein the Accela-Cota was set up as follows:

Spray Gun: Binx Model 61
Fluid Nozzle: 63ASS
Air Cap: 66SD
Nozzle Pressure: 50 psi
Cylinder Pressure: 50 psi
Masterflex Head: 7020-50
Coating Solution Flow Rate: 30 gm/minute
Pan Speed: 12 rpm
Tablet Batch Size: 10 Kg
Inlet Temperature Setting: 60 C.
Outlet Temperature: 38 C.

The invention has industrial applicability for the manufacture of pharmaceutical tablets. The following example illustrates the practice of the invention.

EXAMPLE 1

With stirring 50 g of sodium carboxymethylcellulose available from Aqualon Company as grade 7L2P was slowly added to 940 g deionized water. Mixing was continued until the solution cleared. Then 10 g polyethylene glycol available from Union Carbide as PEG 400, USP was added and mixed until a uniform solution was obtained. Solution viscosity was measured to see if a value between 125 and 150 cps was obtained in order to provide good coating using the Accela-Cota.

Tablets were charged into the pan and allowed to warm up for 15 minutes. Then spraying was begun and ended when acceptable gloss level had been achieved.

Numerous runs were made with various sized oval and round tablet batches. It was observed that acceptable gloss levels were obtained with about 2% or less tablet weight gain, but that improvement in gloss could require coatings ranging from 0.1 to 5.0% weight gain depending on the core composition of the tablet being coated. Thus a large tablet core with a rough surface would require a heavy polymer coating to give high gloss, whereas a small tablet with a very smooth surface would require very little coating to give high gloss.

What is claimed is:

1. A high gloss pharmaceutical tablet comprising of at least one active ingredient in a binder matrix as a core with an outermost coating of sodium carboxymethylcellulose having a degree of substitution (D.S.) between 0.2 and 1.4 and a degree of polymerization (D.P.) between 100 and 400 and a polyethylene glycol plasticizer wherein the outermost coating is applied from a water solution by spray coating.

2. The tablet of claim 1 where the active ingredient is a medicant.

3. The tablet of claim 2 where the outermost coating comprises 0.5 to 5.0% by weight of the total weight of the tablet.

4. The tablet of claim 3 where the polyethylene glycol plasticizer has a molecular weight of about 400.

5. The tablet of claim 4 where the sodium carboxymethylcellulose has a D.S. between 0.5 and 0.9 and a D.P between 200 and 1000.

6. The tablet of claim 5 where the coating contains a colorant.

7. A method for preparing high gloss pharmaceutical tablets comprises the steps:

(1) preparing an aqueous solution of sodium carboxymethylcellulose having a degree of substitution (D.S.) between 0.2 and 1.4 and a degree of polymerization (D.P.) between 100 and 400 and a polyethylene glycol plasticizer; and (2) applying the solution to pharmaceutical tablets by spray coating to provide a weight gain of from 0.5 to 5.0% based on the total weight of the pharmaceutical tablet.

8. The method of claim 7 where the plasticizer is polyethylene glycol with a molecular weight of about 400.

9. The method of claim 8 where the sodium carboxymethylcellulose has a D.S. between 0.5 and 0.9 and a D.P. between 200 and 1000.

10. The method of claim 9 where the weight gain is 1.0 to 2.0%.

* * * * *